United States Patent [19]

Onodera et al.

[11] Patent Number: 5,090,994
[45] Date of Patent: Feb. 25, 1992

[54] HETEROCYCLIC COMPOUNDS AND HERBICIDAL COMPOSITIONS CONTAINING THE COMPOUNDS AS EFFECTIVE COMPONENTS

[75] Inventors: Nobuo Onodera, Hiratsuka; Shinzo Someya, Tokorozawa; Seigo Koura, Nerima; Shigenori Segami, Tokorozawa, all of Japan

[73] Assignee: Agro-kanesho Co., Ltd., Tokyo, Japan

[21] Appl. No.: 447,548

[22] Filed: Dec. 7, 1989

[30] Foreign Application Priority Data

Mar. 2, 1989 [JP] Japan .................. 1-50245

[51] Int. Cl.$^5$ .................... A01N 43/40; C07D 451/00
[52] U.S. Cl. .................................... 71/94; 546/94
[58] Field of Search ............... 546/94; 514/300; 71/94

[56] References Cited

FOREIGN PATENT DOCUMENTS 30-139359 9/1955 Japan .
32-09290 8/1957 Japan .
33-99488 2/1958 Japan .
33-219167 10/1958 Japan .

Primary Examiner—David B. Springer
Assistant Examiner—Robert C. Whittenbaugh
Attorney, Agent, or Firm—Oblon, Spivak, McClelland, Maier & Neustadt

[57] ABSTRACT

A herbicide exhibiting high herbicidal activity against a variety of weeds and being highly safe for useful crops can be obtained through the use of a heterocyclic compound represented by the following general formula (I):

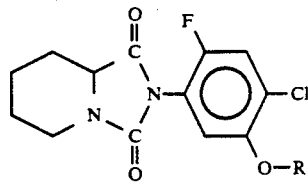

wherein R represents a group represented by the following formula:

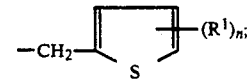

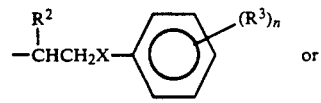

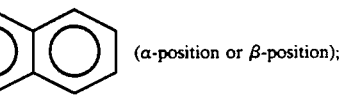

X represents an oxygen atom or a sulfur atom; $R^1$ represents a halogen atom or a lower alkyl group; $R^2$ represents a hydrogen atom or a methyl group; $R^3$ represents a halogen atom, a lower alkyl group, a lower haloalkyl group, a lower alkoxy group, a lower alkylthio group, a cyano group or —COOR$^4$ ($R^4$ is a lower alkyl group, a lower alkoxyalkyl group or a tetrahydrofurfuryl group); m is 0, 1 or 2 and n is 0, 1, 2 or 3.

12 Claims, No Drawings

HETEROCYCLIC COMPOUNDS AND HERBICIDAL COMPOSITIONS CONTAINING THE COMPOUNDS AS EFFECTIVE COMPONENTS

BACKGROUND OF THE INVENTION

1. Field of the Invention

The present invention relates to a novel heterocyclic compound, a method for preparing the compounds and a herbicidal composition containing the same as an effective component.

2. Prior Art Statement

In cultivating field crops and garden crops, the laborious work of weed control has been carried out using a variety of herbicides. However, crops are damaged by these herbicides and the herbicides remain in the environment and cause environmental pollution. Therefore, it has been desired to develop an agricultural chemical which reliably shows high efficacy even if when used in a small amount and which can be used with safety.

There exist a great number of patents concerning herbicides containing heterocyclic compounds, in particular imide type compounds as effective components and a variety of compounds are disclosed therein. Among the many compounds disclosed in known patents, those relatively closely related to the present invention are, for instance, as follows:

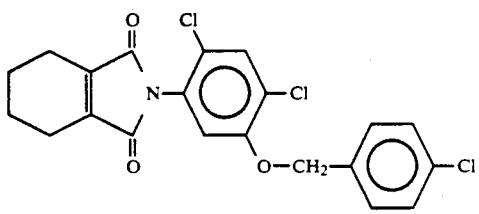

(Japanese Patent Unexamined Patent Application No. 139359/1980);

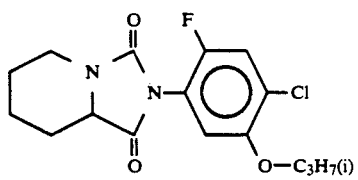

(Japanese Patent Unexamined Patent Application No. 209290/1982);

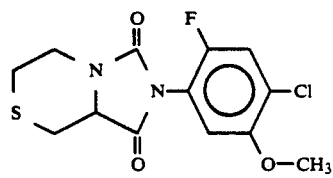

(Japanese Patent Unexamined Patent Application No. 99488/1983);

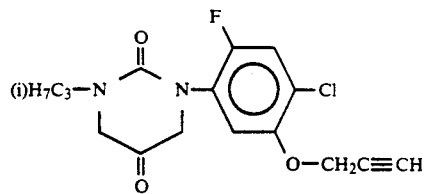

(Japanese Patent Unexamined Patent Application No. 219167/1983); and

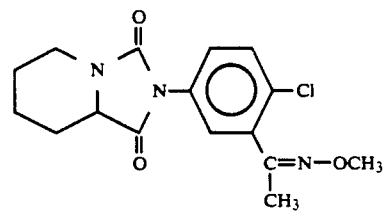

However, these compounds suffer from various problems. For instance, they have only insufficient herbicidal activity and cause crop damage. Thus almost none of the compounds have been put on the market yet.

OBJECT AND SUMMARY OF THE INVENTION

An object of the present invention is to provide a novel compound which shows high herbicidal activity and high safety for crops.

Another object of the present invention is to provide a method for preparing the aforementioned novel compound.

A further object of the present invention is to provide a novel herbicidal composition containing the foregoing novel compound as an effective component.

For developing a useful herbicide which makes it possible to overcome the foregoing problems, the inventors of this invention have conducted various studies on, in particular, heterocyclic compounds and have found that compounds represented by the following general formula (I) (hereunder referred to as "compounds of the present invention") show high herbicidal activity and can safely be used for a variety of crops. They have thus completed the present invention.

More specifically, according to the present invention, there is provided a novel heterocyclic compound represented by the following general formula (I):

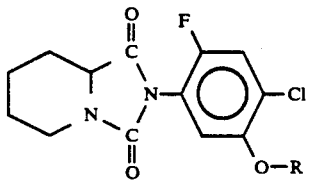

wherein R represents a group represented by the following formula:

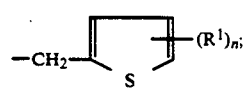

-continued

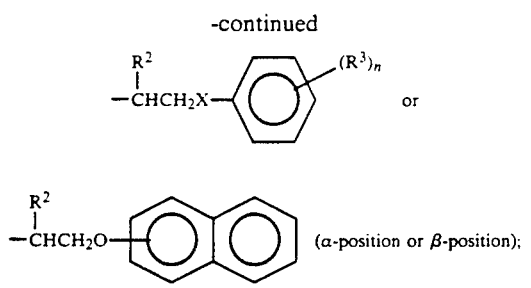

X represents an oxygen atom or a sulfur atom; $R^1$ represents a halogen atom or a lower alkyl group; $R^2$ represents a hydrogen atom or a methyl group; $R^3$ represents a halogen atom, a lower alkyl group, a lower haloalkyl group, a lower alkoxy group, a lower alkylthio group, a cyano group or —COOR$^4$ ($R^4$ is a lower alkyl group, a lower alkoxyalkyl group or a tetrahydrofurfuryl group); m is 0, 1 or 2 and n is 0, 1, 2 or 3.

According to another aspect of the present invention, there is provided a method for preparing a heterocyclic compound represented by the following general formula (I):

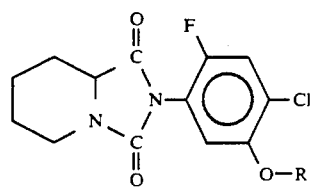

[wherein R represents a group represented by the following formula:

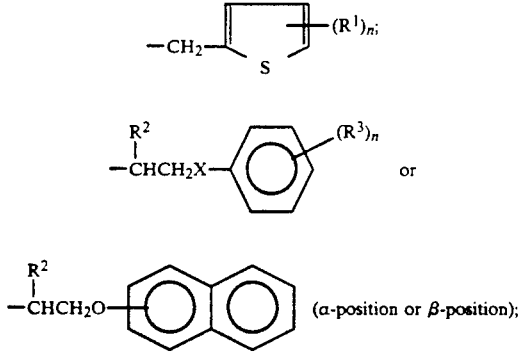

X represents an oxygen atom or a sulfur atom; $R^1$ represents a halogen atom or a lower alkyl group; $R^2$ represents a hydrogen atom or a methyl group; $R^3$ represents a halogen atom, a lower alkyl group, a lower haloalkyl group, a lower alkoxy group, a lower alkylthio group, a cyano group or —COOR$^4$ ($R^4$ is a lower alkyl group, a lower alkoxyalkyl group or a tetrahydrofurfuryl group); m is 0, 1 or 2 and n is 0, 1, 2 or 3], which comprises the step of reacting a compound represented by the following formula:

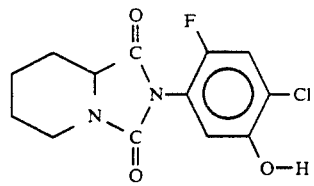

with a compound represented by the following general formula:

R—Y wherein R has the same meaning as that defined above and Y represents a halogen atom or —O—SO$_2$R$^5$ (wherein R$^5$ represents an alkyl group or an aryl group).

According to a further aspect of the present invention, there is provided a herbicidal composition containing a heterocyclic compound represented by the following general formula (I) as an effective component:

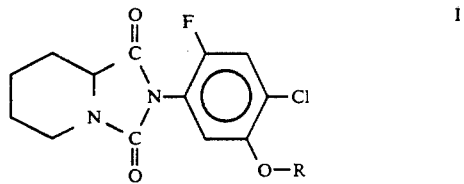

wherein R represents a group represented by the following formula:

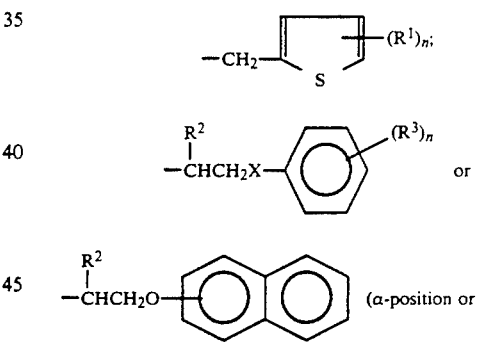

X represents an oxygen atom or a sulfur atom; $R^1$ represents a halogen atom or a lower alkyl group; $R^2$ represents a hydrogen atom or a methyl group; $R^3$ represents a halogen atom, a lower alkyl group, a lower haloalkyl group, a lower alkoxy group, a lower alkylthio group, a cyano group or —COOR$^4$ ($R^4$ is a lower alkyl group, a lower alkoxyalkyl group or a tetrahydrofurfuryl group); m is 0, 1 or 2 and n is 0, 1, 2 or 3.

DETAILED EXPLANATION OF THE INVENTION

The compounds of the present invention are novel compounds which have been synthesized by the inventors of this invention for the first time.

The herbicides of the present invention which comprise the compound of the present invention as an effective component show, as will be explained in Examples given below, excellent herbicidal activity against various weeds that constitute a problem in the water treatment of paddy fields. Such weeds include those belonging to the true grasses such as barnyardgrass, such broad leaf weeds as false pimpernel, spike-flowered rotala, water starwort and ducktongue weed, and such weeds belonging to Cyperus microiria steud family as smallflower umbrellaplant, slender spikrush and water nutgrass. In particular, they exhibit especially excellent herbicidal activity against upland field broad leaf weeds. Examples of such weeds are mustard-plant, Virginia pepperweed, cleaves, bedstraw sp., chickweed, goosefoot, nettle, common groundsel, green amaranth, cocklebur, barnyardgrass, posumbu knotweed and velvetleaf. In addition, gramineous crops such as corn, rice plant and wheat are not damaged by the herbicides of the present invention and the herbicides show high safety.

Typical examples of the compounds of the present invention represented by the general formula (I):

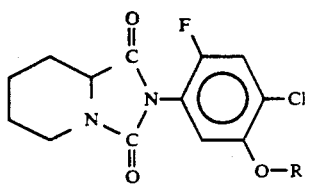
(I)

are as follows: compounds having, as the substituent R, 2-thenyl, 5-chloro-2-thenyl, 2-phenoxyethyl, 2-(2-methylphenoxy)ethyl, 2-(3-methylphenoxy)ethyl, 2-(4-methylphenoxy)ethyl, (2-chlorophenoxy)ethyl, 2-(3-chlorophenoxy)ethyl, 2-(4-chlorophenoxy)ethyl, 2-(4-fluorophenoxy)ethyl, 2-(4-cyanophenoxy)ethyl, 2-(4-ethoxycarbonylphenoxy)ethyl, 2-(3-trifluoromethylphenoxy)ethyl, 2-(4-ethoxyphenoxy)ethyl, 2-(4-methylthiophenoxy)ethyl, 2-(2,4-dimethylphenoxy)ethyl, 2-(3,4-dimethylphenoxy)ethyl, 2-(3,5-dimethylphenoxy)ethyl, 2-(2,4-dichlorophenoxy)ethyl, 2-(3,4-dichlorophenoxy)ethyl, 2-(2-methyl-4-chlorophenoxy)ethyl, 2-(2,3,5-trimethylphenoxy)ethyl, 2-(2,3,6-trimethylphenoxy)ethyl, 2-(3,5-dimethyl-4-chlorophenoxy)ethyl, 2-phenylthioethyl, 2-(4-methylphenylthio)ethyl, 2-(4-chlorophenylthio)ethyl, 2-(1-naphthoxy)ethyl, 2-(2-naphthoxy)ethyl, 2-phenoxy-1-methylethyl, 2-(4-methylphenoxy)-1-methylethyl, 2-(4-chlorophenoxy)-1-methylethyl, 2-(4-isopropylphenoxy)-1-methylethyl, 2-(4-ethoxyphenoxy)-1-methylethyl, 2-(4-methylthiophenoxy)-1-methylethyl, 2-(4-cyanophenoxy)-1-methylethyl, 2-(3,5-dimethylphenoxy)-1-methylethyl, 2-(2,4-dichlorophenoxy)-1-methylethyl, 2-(4-methylphenylthio)-1-methylethyl and 2-(2-naphthoxy)-1-methylethyl.

The compounds of the present invention can be prepared by a method represented by the following reaction formula:

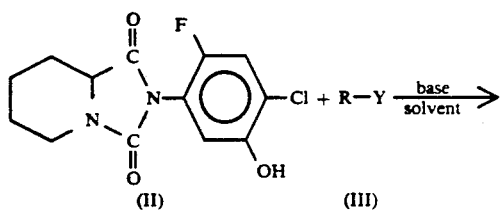

-continued

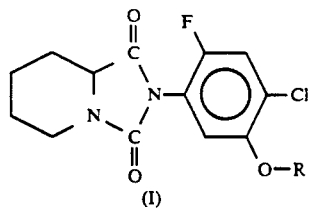
(I)

In these formulas, R and Y have the same meanings as those defined above.

The compounds of the present invention represented by the general formula (I) can be obtained by reacting a compound represented by the formula (II) with a compound represented by the general formula (III) at a temperature ranging from room temperature to the boiling point of a solvent used in the presence of an excess basic material.

The substituent Y of the compound R-Y is preferably a chlorine atom, a bromine atom, —O—SO$_2$CH$_3$ or

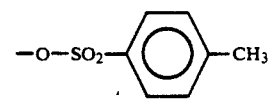

Examples of the solvent are usual inert solvents, for instance, ketones such as acetone; ethers such as tetrahydrofuran, dioxane and dimethoxyethane; esters such as ethyl acetate; aromatic hydrocarbons such as benzene and chlorobenzene; polar solvents such as dimethylformamide and N-methylpyrrolidone. These solvents may be used alone or in combination.

Examples of the basic materials include inorganic bases such as potassium carbonate, sodium carbonate, potassium hydroxide, sodium hydroxide, sodium alcoholates and sodium hydride; and organic amines such as triethylamine and DBU. They are preferably used in excess and generally range from 1.1 to 5.0 times (expressed in molar amount) that of the reactants.

The reaction temperature may be set at any temperature so far as it falls within the range of from room temperature to the boiling point of the solvent used. Preferably, it ranges from 30° to 150° C. and, in particular, 40° to 100° C.

The reaction time may vary depending on the other conditions established, but in general the reaction may be completed within 1 to 10 hours.

The reaction products can be separated from the resultant reaction mixture in an ordinary manner and they may optionally be purified easily by recrystallization or a column chromatography technique.

The compounds of the present invention can also be prepared according to the following reaction scheme:

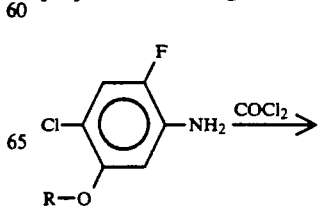

-continued

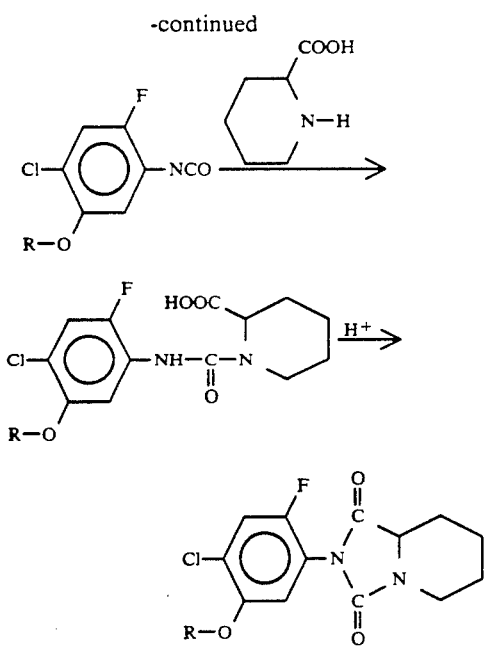

The herbicidal composition of the present invention may be formulated to an emulsible concentrate, oily solution, wettable powder and granules by an ordinary manufacturing method utilizing the aforementioned compounds of the present invention and auxiliary agents for agricultural chemicals commonly used in this field.

These various formulations can practically be used as such or after diluting them with water to a desired concentration.

Examples of the auxiliary agents for agricultural chemicals are diluents, surfactants, stabilizers, adhesive agents, propellants for aerosol, synergists, solid carriers, effect-retardants, dispersionstabilizing agents. Specific examples of the diluents are water, hydrocarbons, alcohols, ethers, alcohol ethers, ketones, esters, amides, and sulfoxides. Specific examples of the solid carriers include inorganic powder and particles such as quick lime, magnesium lime, gypsum, calcium carbonate, siliceous earth, perlite, pumice stone, diatomaceous earth, alumina, zeolite, mineral clay (e.g., talc, vermiculite and kaolinite); plant powder and particles such as starches, grains and dextrose; and synthetic resin powder such as phenol resins, carbon resins and vinyl chloride resins. Specific examples of the surfactants are anionic surfactants such as alkyl sulfuric acid esters, aryl sulfonic acids, succinic acid salts and polyethylene glycol alkyl aryl ether sulfates; cationic surfactants such as alkylamines and polyoxyethylene alkylamines; nonionic surfactants such as polyoxyethylene glycol ethers, polyoxyethylene glycol esters and polyhydric alcohol esters and amphoteric surfactants.

Examples of specific preparations are as follows:

Example of Preparation 1 (Emulsifiable Concentrate)

20 Parts by weight of an effective component, 60 parts by weight of xylene and 20 parts by weight of Sorpol 2806B (trade name of a surfactant available from TOHO CHEMICAL INDUSTRIES CO., LTD.) are uniformly admixed with stirring to obtain an emulsifiable concentrate.

Example of Preparation 2 (Wettable Powder)

10 Parts by weight of an effective component, 87 parts by weight of Zieclite, 1.5 parts by weight of Neopelex powder (trade name; available from KAO CORPORATION) and 1.5 parts by weight of Sorpol 800A (trade name of a surfactant available from TOHO CHEMICAL INDUSTRIES CO., LTD.) are comminuted and mixed together to form a wettable powder.

The herbicides of the present invention can be used in a manner similar to that for conventional herbicides. For instance, they may be used for treating soil prior to germination of upland field weeds or at the early germination stage thereof. Alternatively, for paddy field weeds, the herbicides of the present invention may be used to treat soil after implantation and rooting of, for instance, rice plant and prior to or immediately after the germination of weeds.

The dose of the herbicides of the present invention may properly be selected depending on various factors such as method of application, purposes, time and the state of weed development, but in general, it ranges from 0.01 to 10 kg, preferably 0.05 to 5 kg per hectare, expressed in the amount of the effective component.

The present invention will hereinafter be explained in more detail with reference to the following Examples, but the present invention is not limited to these specific Examples.

EXAMPLE 1

Preparation of N-[4-chloro-2-fluoro-5-(5-chloro-2-thenyloxy)phenyl]-1,2-piperidinedicarboximide (Compound No. 1)

0.83 g of N-(4-chloro-2-fluoro-5-hydroxyphenyl)-1,2-piperidinedicarboximide was stirred together with 1.40 g of potassium carbonate, 10 ml of dimethoxyethane and 0.42 g of 5-chloro-2-thenyl chloride at 60° to 65° C. for 5 hours. After letting the reaction mixture stand to cool, water was added thereto to precipitate out crystals, followed by filtering off the crystals and washing them with water to thus obtain crude crystals. The crystals were purified with ether to obtain 0.70 g of the title compound.

M.P. = 135°~137° C.

EXAMPLE 2

Preparation of N-[4-chloro-2-fluoro-5-(2-phenoxyethoxy)phenyl]-1,2-piperidinedicarboximide (Compound No. 2)

0.80 g of N-(4-chloro-2-fluoro-5-hydroxyphenyl)-1,2-piperidinedicarboximide was refluxed together with 1.50 g of potassium carbonate, 10 ml of acetone and 0.65 g of 2-phenoxyethyl bromide for 8 hours. After letting the reaction mixture stand to cool, water was added thereto to precipitate out crystals, followed by filtering the crystals and washing them with water to obtain crude crystals. Then, the crystals were purified with n-hexane to thus obtain 0.64 g of the title compound.

M.P. = 133°~135° C.

EXAMPLE 3

Preparation of
N-[4-chloro-2-fluoro-5-{2-(4-cyanophenoxy)ethoxy}phenyl]-1,2-piperidinedicarboximide (Compound No. 7)

0.80 g of N-(4-chloro-2-fluoro-5-hydroxyphenyl)-1,2-piperidinedicarboximide was stirred together with 1.50 g of potassium carbonate, 10 ml of dimethylformamide and 0.72 g of 2-(4-cyanophenoxy)ethyltosylate at 70° to 75° C. for 6 hours. After letting the reaction mixture stand to cool, water was added, followed by extracting the mixture with benzene, washing with water, drying over anhydrous magnesium sulfate and then concentrating the extract under a reduced pressure. The resulting residue was purified through silica gel column chromatography to thus obtain 0.54 g of the title compound.
M.P.=156.5°~157.5° C.

EXAMPLE 4

Preparation of
N-[4-chloro-2-fluoro-5-{2-(3,4-dimethylphenoxy)ethoxy}phenyl]-1,2-piperidinedicarboximide (Compound No. 11)

0.75 g of N-(4-chloro-2-fluoro-5-hydroxyphenyl)-1,2-piperidinedicarboximide was refluxed together with 1.39 g of potassium carbonate, 15 ml of dimethoxyethane and 0.69 g of 2-(3,4-dimethylphenoxy)ethyl bromide for 5 hours. After letting the reaction mixture stand to cool, water was added, followed by extracting the mixture with benzene, washing with water, drying over anhydrous magnesium sulfate and then concentrating the extract under a reduced pressure. The resulting residue was purified through silica gel column chromatography to thus obtain 0.54 g of the title compound.
M.P.=100°~103° C.

EXAMPLE 5

Preparation of
N-[4-chloro-2-fluoro-5-{2-(4-chlorophenoxy)-1-methylethoxy}phenyl]-1,2-piperidinedicarboximide (Compound No. 15)

0.75 g of N-(4-chloro-2-fluoro-5-hydroxyphenyl)-1,2-piperidinedicarboximide was refluxed together with 1.39 g of potassium carbonate, 15 ml of dimethoxyethane and 0.72 g of 2-(4-chlorophenoxy)-1-methylethyl tosylate for 4 hours. After letting the reaction mixture stand to cool, water was added, followed by extracting the mixture with benzene, washing with water, drying over anhydrous magnesium sulfate and then, concentrating the extract under a reduced pressure. The resulting residue was purified through silica gel column chromatography to thus obtain 0.69 g of the title compound.
M.P.=123.5°~125° C.

Typical examples of the compounds of the present invention prepared according to procedures similar to those in the foregoing Examples (inclusive of those prepared in the foregoing Examples) are listed in the following Table I.

TABLE I

Typical Examples of the Compounds of the Invention:

| Comp. No. | R | Physical Const. mp (°C.) |
|---|---|---|
| 1 | $-CH_2-\underset{S}{\text{(thiophene)}}-Cl$ | 135 to 137 |
| 2 | $-CH_2CH_2O-$(phenyl) | 133 to 135 |
| 3 | $-CH_2CH_2O-$(phenyl)$-CH_3$ | 104 to 106 |
| 4 | $-CH_2CH_2O-$(phenyl with $CH_3$) | 119 to 121 |
| 5 | $-CH_2CH_2O-$(phenyl)$-Cl$ | 138.5 to 140 |
| 6 | $-CH_2CH_2O-$(phenyl)$-F$ | 144.8 to 146.4 |
| 7 | $-CH_2CH_2O-$(phenyl)$-CN$ | 156.5 to 157.5 |
| 8 | $-CH_2CH_2O-$(phenyl with Cl) | 157 to 159 |
| 9 | $-CH_2CH_2O-$(phenyl with $CH_3$) | resinous form IR (cm$^{-1}$): C=O: 1782, 1728 3H: 795 |
| 10 | $-CH_2CH_2O-$(phenyl with two $CH_3$) | 162.5 to 164 |

TABLE I-continued

Typical Examples of the Compounds of the Invention:

[Structure: bicyclic imide with piperidine fused to N-aryl ring bearing F, Cl, and O—R substituents]

| Comp. No. | R | Physical Const. mp (°C.) |
|---|---|---|
| 11 | —CH$_2$CH$_2$O—(phenyl with 2-CH$_3$, 4-CH$_3$) | 100 to 103 |
| 12 | —CH$_2$CH$_2$O—(phenyl with 2-CH$_3$, 3-CH$_3$) | resinous form IR (cm$^{-1}$): C=O: 1782, 1728 2H: 819 |
| 13 | —CH(CH$_3$)CH$_2$O—(phenyl) | resinous form IR (cm$^{-1}$): C=O: 1782, 1725 5H: 756 |
| 14 | —CH(CH$_3$)CH$_2$O—(phenyl-F) | resinous form IR (cm$^{-1}$): C=O: 1782, 1728 2H: 828 |
| 15 | —CH(CH$_3$)CH$_2$O—(phenyl-Cl) | 123.5 to 125 |
| 16 | —CH(CH$_3$)CH$_2$O—(phenyl-CH$_3$) | 99 to 101 |
| 17 | —CH(CH$_3$)CH$_2$O—(phenyl-C$_3$H$_7$(i)) | 88.5 to 91 |
| 18 | —CH(CH$_3$)CH$_2$O—(phenyl-OC$_2$H$_5$) | resinous form IR (cm$^{-1}$): C=O: 1782, 1728 2H: 819 |
| 19 | —CH(CH$_3$)CH$_2$O—(phenyl-SCH$_3$) | 131.5 to 134 |
| 20 | —CH$_2$CH$_2$O—(naphthyl) | 136.5 to 139 |

EXAMPLE 6

Test on Treatment of Soil for Rice Plant Implantation

In 1/5000 Are Wagner Pots, soil from a paddy field was packed, followed by sowing the paddy field with seeds of weeds listed in Table II. After puddling the bed, rice plant seedlings at their 2-leaf stage (Sasanishiki sp.) were transplanted and maintained under a flooded condition of about 4.0 cm of water. The herbicides of this invention prepared according to Example of Preparation 1 were diluted with a desired quantity of water and were sprayed on the water surface uniformly in the amounts listed in Table II at the early stage of development of barnyardgrass, broad leaf weeds or the like. As a control, there was used N-(4-chloro-2-fluoro-5-isopropoxyphenyl)-3,4,5,6-tetrahydrophthalimide as disclosed in Japanese Patent Unexamined Application No. 163365/1982. The growth condition of weeds and crops was observed 20 days after the treatment with the agricultural chemicals and the results summarized in Table II were obtained. In Table II, the herbicidal efficacy is estimated according to the following 6-stage evaluation. Moreover, the damages to the crops from the agricultural chemicals used were also estimated on the same standard.

| | | |
|---|---|---|
| 0 | control rate | 0 to 9% |
| 1 | control rate | 10 to 29% |
| 2 | control rate | 30 to 49% |
| 3 | control rate | 50 to 69% |
| 4 | control rate | 70 to 89% |
| 5 | control rate | 90 to 100% |

TABLE II

| Comp. No. | Dose (g/a) | Rice Plant | Barnyardgrass | Smallflower umbrellaplant | ducktongue weed | annual broad leaf weed |
|---|---|---|---|---|---|---|
| 1 | 10 | 0 | 5 | 5 | 5 | 5 |
| 1 | 2.5 | 0 | 5 | 5 | 5 | 4 |
| 1 | 0.625 | 0 | 5 | 5 | 5 | 4 |
| 2 | 10 | 0 | 5 | 5 | 5 | 5 |
| 2 | 2.5 | 0 | 5 | 5 | 5 | 5 |
| 2 | 0.625 | 0 | 5 | 5 | 5 | 5 |
| 3 | 10 | 0 | 5 | 5 | 5 | 5 |
| 3 | 2.5 | 0 | 5 | 5 | 5 | 5 |
| 3 | 0.625 | 0 | 5 | 5 | 5 | 5 |
| 4 | 10 | 0 | 5 | 5 | 5 | 5 |
| 4 | 2.5 | 0 | 5 | 5 | 5 | 5 |
| 4 | 0.625 | 0 | 5 | 5 | 5 | 5 |
| 5 | 10 | 0 | 5 | 5 | 5 | 5 |
| 5 | 2.5 | 0 | 5 | 5 | 5 | 5 |
| 5 | 0.625 | 0 | 5 | 5 | 5 | 5 |
| 6 | 10 | 1 | 5 | 5 | 5 | 5 |
| 6 | 2.5 | 0 | 5 | 5 | 5 | 5 |
| 6 | 0.625 | 0 | 5 | 5 | 5 | 5 |
| 7 | 10 | 0 | 5 | 5 | 5 | 5 |
| 7 | 2.5 | 0 | 5 | 5 | 5 | 4 |
| 7 | 0.625 | 0 | 4 | 5 | 4 | 3 |
| 8 | 10 | 0 | 5 | 5 | 5 | 5 |
| 8 | 2.5 | 0 | 5 | 5 | 5 | 5 |
| 8 | 0.625 | 0 | 4 | 5 | 5 | 5 |
| 9 | 10 | 0 | 5 | 5 | 5 | 5 |
| 9 | 2.5 | 0 | 5 | 5 | 5 | 5 |
| 9 | 0.625 | 0 | 5 | 5 | 5 | 5 |
| 10 | 10 | 0 | 5 | 5 | 5 | 5 |
| 10 | 2.5 | 0 | 5 | 5 | 5 | 5 |
| 10 | 0.625 | 0 | 5 | 5 | 5 | 5 |
| 11 | 10 | 0 | 5 | 5 | 5 | 5 |
| 11 | 2.5 | 0 | 5 | 5 | 5 | 5 |
| 11 | 0.625 | 0 | 5 | 5 | 5 | 5 |
| 12 | 10 | 0 | 5 | 5 | 5 | 5 |
| 12 | 2.5 | 0 | 5 | 5 | 5 | 5 |
| 12 | 0.625 | 0 | 5 | 5 | 5 | 5 |
| 13 | 10 | 0 | 5 | 5 | 5 | 5 |
| 13 | 2.5 | 0 | 5 | 5 | 5 | 5 |
| 13 | 0.625 | 0 | 5 | 5 | 5 | 5 |
| 14 | 10 | 0 | 5 | 5 | 5 | 5 |
| 14 | 2.5 | 0 | 5 | 5 | 5 | 5 |
| 14 | 0.625 | 0 | 4 | 5 | 5 | 5 |

TABLE II-continued

| Comp. No. | Dose (g/a) | Rice Plant | Barn- yard- grass | Small- flower umbrella- plant | duckton- gue weed | annual broad leaf weed |
|---|---|---|---|---|---|---|
| 15 | 10 | 0 | 5 | 5 | 5 | 5 |
| 15 | 2.5 | 0 | 5 | 5 | 5 | 5 |
| 15 | 0.625 | 0 | 5 | 5 | 5 | 5 |
| 16 | 10 | 0 | 5 | 5 | 5 | 5 |
| 16 | 2.5 | 0 | 5 | 5 | 5 | 5 |
| 16 | 0.625 | 0 | 5 | 5 | 5 | 5 |
| 17 | 10 | 0 | 5 | 5 | 5 | 5 |
| 17 | 2.5 | 0 | 5 | 5 | 4 | 5 |
| 17 | 0.625 | 0 | 5 | 5 | 3 | 5 |
| 18 | 10 | 0 | 5 | 5 | 5 | 5 |
| 18 | 2.5 | 0 | 5 | 5 | 5 | 5 |
| 18 | 0.625 | 0 | 5 | 5 | 5 | 4 |
| 19 | 10 | 0 | 5 | 5 | 5 | 5 |
| 19 | 2.5 | 0 | 5 | 5 | 5 | 4 |
| 19 | 0.625 | 0 | 5 | 4 | 5 | 3 |
| 20 | 10 | 0 | 5 | 5 | 5 | 5 |
| 20 | 2.5 | 0 | 5 | 5 | 5 | 5 |
| 20 | 0.625 | 0 | 5 | 5 | 5 | 5 |
| Comp. Ex. | 10 | 2 | 3 | 4 | 5 | 5 |
| | 2.5 | 2 | 2 | 3 | 4 | 4 |
| | 0.625 | 1 | 1 | 2 | 2 | 3 |

Comp. Compound:
N-(4-chloro-2-fluoro-5-isopropoxyphenyl)-3,4,5,6-tetrahydrophthalimide.

EXAMPLE 7

Foliage Treatment

Upland soil was packed in plastic vats measuring 22 cm × 16 cm, followed by sowing the upland soil with seeds of wheat, corn and soybean in a definite amount and covering the seeds with soil containing seeds of weeds such as velvetleaf, green amaranth and cocklebur in a thickness of about 1 cm. The foregoing compounds were sprayed in an amount listed in Table III when the crops such as wheat reached 2 to 2.5 leaf stage. The growth conditions of the crops and the weeds were observed 14 days after the spraying of the compounds and the results listed in Table III were observed.

As a control compound, the same compound as that used in Example 6 was employed and the herbicidal efficacy of each compound and damages of the crops from the compounds used were also evaluated in the same manner as in Example 6.

TABLE III

| Comp. No. | Dose (g/10 a) | Soy- bean | Wheat | Corn | Green ama- ranth | Vel- vet- leaf | Cockle- bur |
|---|---|---|---|---|---|---|---|
| 1 | 20 | 1 | 0 | 0 | 5 | 5 | 5 |
| 1 | 10 | 0 | 0 | 0 | 5 | 5 | 5 |
| 2 | 20 | 1 | 0 | 0 | 5 | 5 | 5 |
| 2 | 10 | 0 | 0 | 0 | 5 | 5 | 4 |
| 3 | 20 | 1 | 0 | 0 | 5 | 5 | 5 |
| 3 | 10 | 0 | 0 | 0 | 5 | 5 | 5 |
| 4 | 20 | 0 | 0 | 0 | 5 | 5 | 4 |
| 4 | 10 | 0 | 0 | 0 | 5 | 5 | 3 |
| 5 | 20 | 0 | 0 | 0 | 5 | 5 | 5 |
| 5 | 10 | 0 | 0 | 0 | 5 | 5 | 4 |
| 6 | 20 | 0 | 0 | 0 | 5 | 5 | 4 |
| 6 | 10 | 0 | 0 | 0 | 5 | 5 | 3 |
| 7 | 20 | 0 | 0 | 0 | 5 | 5 | 5 |
| 7 | 10 | 0 | 0 | 0 | 5 | 5 | 4 |
| 8 | 20 | 0 | 0 | 0 | 5 | 5 | 4 |
| 8 | 10 | 0 | 0 | 0 | 5 | 5 | 3 |
| 9 | 20 | 1 | 0 | 0 | 5 | 5 | 5 |
| 9 | 10 | 0 | 0 | 0 | 5 | 5 | 5 |
| 10 | 20 | 0 | 0 | 0 | 5 | 5 | 5 |
| 10 | 10 | 0 | 0 | 0 | 5 | 5 | 4 |
| 11 | 20 | 0 | 0 | 0 | 5 | 5 | 5 |
| 11 | 10 | 0 | 0 | 0 | 5 | 5 | 5 |
| 12 | 20 | 0 | 0 | 0 | 5 | 5 | 5 |
| 12 | 10 | 0 | 0 | 0 | 5 | 5 | 5 |
| 13 | 20 | 1 | 0 | 0 | 5 | 5 | 5 |
| 13 | 10 | 0 | 0 | 0 | 5 | 5 | 5 |
| 14 | 20 | 0 | 0 | 0 | 5 | 5 | 5 |
| 14 | 10 | 0 | 0 | 0 | 5 | 5 | 5 |
| 15 | 20 | 0 | 0 | 0 | 4 | 5 | 4 |
| 15 | 10 | 0 | 0 | 0 | 2 | 4 | 3 |
| 16 | 20 | 0 | 0 | 0 | 5 | 5 | 5 |
| 16 | 10 | 0 | 0 | 0 | 5 | 5 | 4 |
| 17 | 20 | 0 | 0 | 0 | 5 | 5 | 5 |
| 17 | 10 | 0 | 0 | 0 | 4 | 4 | 4 |
| 18 | 20 | 1 | 0 | 0 | 5 | 5 | 5 |
| 18 | 10 | 0 | 0 | 0 | 5 | 5 | 5 |
| 19 | 20 | 0 | 0 | 0 | 5 | 5 | 5 |
| 19 | 10 | 0 | 0 | 0 | 4 | 5 | 4 |
| 20 | 20 | 0 | 0 | 0 | 5 | 5 | 5 |
| 20 | 10 | 0 | 0 | 0 | 4 | 5 | 4 |
| Comp. Ex. | 20 | 4 | 2 | 2 | 5 | 5 | 4 |
| | 10 | 3 | 1 | 1 | 3 | 4 | 3 |

According to the present invention, there can be provided novel compounds having excellent herbicidal activity and high safety as herbicides and methods for preparing such compounds. In addition, the herbicides of the present invention containing such compounds as effective components exhibit high herbicidal activity which makes it possible to reliably eradicate of various weeds. Moreover, they are highly safe for various useful crops and, therefore, they can be used in paddy fields and/or upland fields without damaging, in particular, rice plant, or wheat and corn as upland field crops.

We claim:

1. A heterocyclic compound represented formula (I):

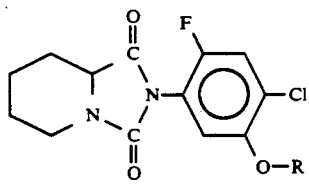

wherein R is:

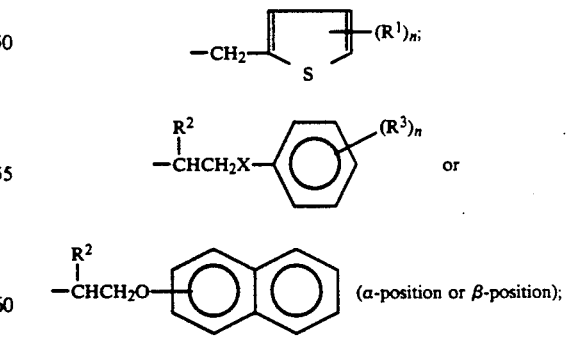

(α-position or β-position);

X is an oxygen atom or a sulfur atom; $R^1$ is a halogen atom or a lower alkyl group; $R^2$ is a hydrogen atom or a methyl group; $R^3$ represents a halogen atom, a lower alkyl group, a lower haloalkyl group, a lower alkoxy group, a lower alkylthio group, a cyano group or —COOR$^4$ ($R^4$ is a lower alkyl group, a lower alkoxyalkyl group or a tetrahydrofurfuryl group); m is 0, 1 or 2 and n is 0, 1, 2 or 3.

2. The heterocyclic compound according to claim 1 which is N-[4-chloro-2-fluoro-5-{2-(4-fluorophenoxy)ethoxy}phenyl]-1,2-piperidinedicarboximide.

3. The heterocyclic compound according to claim 1 which is N-[4-chloro-2-fluoro-5-{2-(3-methylphenoxy)ethoxy}phenyl]-1,2-piperidinedicarboximide.

4. The heterocyclic compound according to claim 1 which is N-[4-chloro-2-fluoro-5-{2-(3,4-dimethylphenoxy)ethoxy}phenyl]-1,2-piperidinedicarboximide.

5. The heterocyclic compound according to claim 1 which is N-[4-chloro-2-fluoro-5-{2-(2,4-dimethylphenoxy)ethoxy}phenyl]-1,2-piperidinedicarboximide.

6. The heterocyclic compound according to claim 1 which is N-[4-chloro-2-fluoro-5-{2-(4-methylphenoxy)-1-methylethoxy}phenyl]-1,2-piperidinedicarboximide.

7. A herbicidal composition containing a heterocyclic compound of the formula (I):

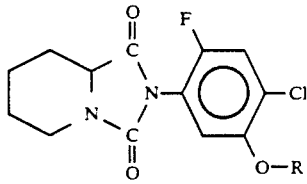

I

[wherein R of the formula:

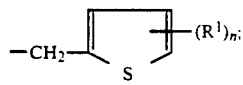

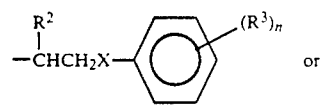

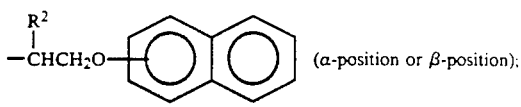

(α-position or β-position);

X is an oxygen atom or a sulfur atom; $R^1$ is a halogen atom or a lower alkyl group; $R^2$ is a hydrogen atom or a methyl group; $R^3$ is a halogen atom, a lower alkyl group, a lower haloalkyl group, a lower alkoxy group, a lower alkylthio group, a cyano group or —$COOR^4$ ($R^4$ is a lower alkyl group, a lower alkoxyalkyl group or a tetrahydrofurfuryl group); m is 0, 1 or 2 and n is 0, 1, 2 or 3] as an effective component in a herbicidally effective amount together with a proper carrier.

8. The herbicidal composition according to claim 7 wherein the compound is N-[4-chloro-2-fluoro-5-{2-(4-fluorophenoxy)ethoxy}phenyl]-1,2-piperidinedicarboximide.

9. The herbicidal composition according to claim 7 wherein the compound is N-[4-chloro-2-fluoro-5-{2-(3-methylphenoxy)ethoxy}phenyl]-1,2-piperidinedicarboximide.

10. The herbicidal composition according to claim 7 wherein the compound is N-[4-chloro-2-fluoro-5-{2-(3,4-dimethylphenoxy)ethoxy}phenyl]-1,2-piperidinedicarboximide.

11. The herbicidal composition according to claim 7 wherein the compound is N-[4-chloro-2-fluoro-5-{2-(2,4-dimethylphenoxy)ethoxy}phenyl]-1,2-piperidinedicarboximide.

12. The herbicidal composition according to claim 7 wherein the compound is N-[4-chloro-2-fluoro-5-{2-(4-methylphenoxy)-1-methylethoxy}phenyl]-1,2-piperidinedicarboximide.

* * * * *